United States Patent [19]

Bergfeld et al.

[11] Patent Number: 4,853,475
[45] Date of Patent: Aug. 1, 1989

[54] PROCESS FOR SYNTHESIZING ALKYLENE BISDITHIOCARBAMATES OR THE AMMONIA ADDUCTS THEREOF AS WELL AS MIXTURES THAT CAN BE SYNTHESIZED THEREBY

[75] Inventors: Manfred Bergfeld, Erlenbach-Mechenhard; Ludwig Eisenhuth, Obernburg, both of Fed. Rep. of Germany

[73] Assignee: Akzo N.V., Arnhem, Netherlands

[21] Appl. No.: 911,364

[22] Filed: Sep. 25, 1986

[30] Foreign Application Priority Data

Sep. 26, 1985 [DE] Fed. Rep. of Germany ....... 3534246

[51] Int. Cl.$^4$ ............................................. C07F 11/00
[52] U.S. Cl. ..................................................... 556/50
[58] Field of Search ........................ 260/513.5; 556/50

[56] References Cited

U.S. PATENT DOCUMENTS 2,317,765 4/1943 Hester .................................... 167/22
2,504,404 4/1950 Flenner .................................. 167/22
2,844,623 7/1958 Fike ....................................... 260/500

FOREIGN PATENT DOCUMENTS 195440 2/1958 Austria .
1202266 10/1965 Fed. Rep. of Germany .
795142 5/1958 United Kingdom .

OTHER PUBLICATIONS

Cipac Handbook, 1970, I, pp. 463–467.

*Primary Examiner*—Nicky Chan
*Attorney, Agent, or Firm*—Oliff & Berridge

[57] ABSTRACT

The invention relates to a process for synthesizing alkylene bisdithiocarbamates or the ammonia adducts thereof as well as mixtures that can be synthesized thereby. The starting materials are carbon disulfide, ammonia, a diamine and a metal oxide, which may be manganese(II) oxide, or the hydrate or hydroxide thereof. The metal oxide, its hydrate or hydroxide thereof is allowed to react either with a mixture syntheiszed from an alkylenediamine, carbon disulfide and ammonia in water, or with an aqueous solution of the ammonium alkylene bisdithiocarbamate. The concentration of the individual starting materials both relative to each other and to water is of prime importances as to which compounds in particular are ultimately obtained.

7 Claims, 2 Drawing Sheets

PROCESS FOR SYNTHESIZING ALKYLENE BISDITHIOCARBAMATES OR THE AMMONIA ADDUCTS THEREOF AS WELL AS MIXTURES THAT CAN BE SYNTHESIZED THEREBY

BACKGROUND OF THE INVENTION

A. Field of the Invention

The invention relates to a process for synthesizing alkylene bisdithiocarbamates or the ammonia adducts thereof starting from carbon disulfide, ammonia, a diamine and a metal oxide or the hydrate or hydroxide thereof. The invention also relates to mixtures which can be synthesized by the process. The product in question is mainly manganese ethylene bisdithiocarbamate, also known as "Maneb", and the ammonia adducts thereof.

B. Description of the Prior Art

Maneb and the ammonia-containing adducts of Maneb are known as fungicides. The synthesis of these compounds can be achieved by first reacting ethylenediamine with carbon disulfide and a strong base, e.g., sodium hydroxide, to obtain sodium bisethylenedithiocarbamate as described in U.S. Pat. No. 2,317,765. Aqueous solutions of such salts are then reacted with water-soluble manganese compounds, such as manganese sulfate or manganese chloride as described in U.S. Pat. No. 2,504,404. The water-insoluble manganese ethylene bisdithiocarbamate then precipitates out. By means of this process, Maneb is now being synthesized on an industrial scale.

In addition, West German Pat. No. 1,202,266 teaches a process for synthesizing ammonia-containing adducts of the manganese salt of ethylene bisdithiocarbamic acid, wherein a water-soluble salt, e.g., an ammonium salt of ethylene bisdithiocarbamic acid, is reacted with a water-soluble manganese salt, e.g., manganese sulfate, in the presence of ammonia. This patent also teaches that Maneb forms stable addition products with ammonia. They have much greater stability during storage than Maneb. Moreover, they have good fungicidal efficacy and better compatibility for plants than Maneb itself. A teaching of how the individual ammonia adducts having 1 or 2 ammonia molecules per manganese atom are synthesized is not given.

Finally, Austrian Pat. No. 195,440 teaches a process for synthesizing poorly water-soluble, crystalline ethylene bisdithiocarbamates of multivalent metals, wherein the metal oxide is allowed to react either with the necessary quantity of starting materials needed for the formation of ammonium dithiocarbamate or with an aqueous solution of ammonium ethylene bisdithiocarbamate. Of the metal oxides, only zinc oxide is specifically named. Also, in the examples, only zinc oxide is used for synthesizing zinc ethylene bisdithiocarbamate. No mention is made of ammonia adducts and the detailed synthesis thereof.

SUMMARY OF THE INVENTION

The object of the invention is to develop a process for synthesizing alkylene bisdithiocarbamates which makes it possible, without isolating an intermediate compound, to synthesize both the ammonia-free compounds and the ammonia-containing adducts with up to 2 moles of ammonia per 1 mole of alkylene bisdithiocarbamate purposefully and in a simple and economically favorable way, starting from carbon disulfide, ammonia, a diamine and a metal compound. Preferably, the alkylene bisdithiocarbamates are synthesized from an aqueous mixture of alkylenediamine, carbon disulfide and ammonia having a molar ratio of $1/\leqq 2$, respectively. In a still more preferred embodiment, the molar ratio of the alkylenediamine/carbon disulfide/ammonia aqueous mixture is $1/0.5-1$, respectively.

The invention is essentially characterized by the fact that, from the plurality of possible metal oxides or the hydrates or hydroxides thereof, manganese oxide or the hydrate or hydroxide thereof is selected and reacted directly or indirectly with carbon disulfide, ammonia and an alkylenediamine in an aqueous medium. Moreover, of prime importance with regard to the synthesis of the particular individual compounds is the concentrations of the individual starting materials, which are used both relative to each other and to water.

DETAILED DESCRIPTION OF THE INVENTION

The process of the invention can be performed either in a single stage or in two stages. In the two-stage process, the ammonium alkylene bisdithiocarbamate is first synthesized in aqueous solution from the alkylenediamine, carbon disulfide and ammonia, as exemplified in French Pat. No. 1,099,969 and in U.S. Pat. No. 2,844,623. In a second stage, the aqueous solution of the ammonium alkylene bisdithiocarbamate is reacted with manganese oxide in powdered form, care being taken to ensure good dispersion of the manganese oxide in the aqueous phase. This can be achieved, for example, by vigorous stirring. Obviously, it is also possible to synthesize an aqueous suspension of the manganese oxide first and then to add the ammonium salt thereto.

Ammonium alkylene bisdithiocarbamate and manganese (II) oxide can be reacted in both stoichiometric and in non-stoichiometric ratios, an excess of ammonium alkylene bisdithiocarbamate being preferred in the latter case.

The quantity of water is best adjusted to such a level that a readily mixable suspension is obtained. It is advisable that at least an adequate amount of water be present during the reaction so that the initial concentration of the ammonium alkylene bisdithiocarbamate is at most 10 moles per liter of water.

The reaction can be represented by the following equation:

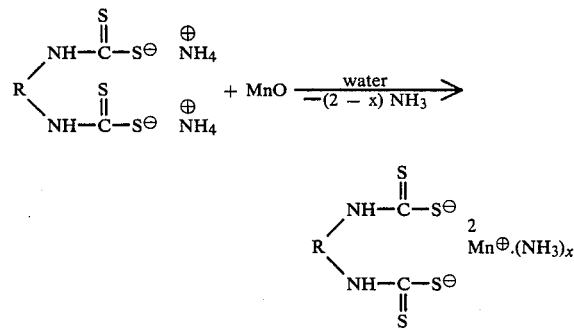

wherein R is $C_2H_4$ to $C_6H_{12}$ and X is 0 to 2.

The ammonia content of the resulting product depends on the concentration of the ammonium alkylene bisdithiocarbamate in the reaction system. The lower the concentration of ammonium alkylene bisdithiocarbamate, i.e., the higher the water concentration in the system, the lower the ammonia content in the resulting product. With very high water concentrations, it is possible to obtain a practically ammonia-free product.

The relationships between the concentration of ammonium alkylene bisdithiocarbamate and the ammonia content of the resulting product are summarized in Table 1, when using ammonium ethylene bisdithiocarbamate (AEBDC):

TABLE 1

| AEBDC (moles/liter water) | Product analysis (moles $NH_3$/2 moles $CS_2$) |
|---|---|
| 0.02 | 0 |
| 0.6 | 1 |
| 1.1 | 1.1 |
| 4.5 | 2 |

The reaction can be performed between room temperature and 60° C.

The reaction time is from 1 to 6 hours, depending on reaction temperature and stirring intensity.

The reaction can be shortened by using the most finely divided, finely powdered manganese oxide possible. The use of a suspending agent is also advantageous.

After the reaction has ended, the reaction mixture is filtered, washed, if necessary, and dried.

A particularly unexpected finding was that, according to the invention, it is possible in a simple and economic way to synthesize the manganese alkylene bisdithiocarbamate and the ammonia-containing adducts thereof by a judicious choice of the ammonium alkylene bisdithiocarbamate concentration.

In the one-stage process, the carbon disulfide is first added to an aqueous solution of alkylenediamine and ammonia with vigorous stirring, during which the temperature is generally maintained below 40° C., and especially below 30° C. To a mixture synthesized in this way from alkylenediamine, carbon disulfide and ammonia, the manganese oxide is then added as a powder or as a suspension and stirring is continued, during which the reaction temperature can be in the range of 30° to 60° C. Depending on reaction temperature and stirring intensity, the reaction time is 1 to 6 hours. The reaction product is filtered off, washed with water if necessary, and dried.

The relationships between the molar ratios of alkylenediamine, carbon disulfide and ammonia, on the one hand, and the adduct formation, on the other, are summarized in Table 2, when using ethylenediamine.

TABLE 2

| Ethylenediamine/$CS_2$/$NH_3$ (moles/moles/moles) | | | moles $NH_3$/ ltr $H_2O$ | Product analysis (moles $NH_3$/ 2 moles $CS_2$) |
|---|---|---|---|---|
| 1 | 2 | 1 | 0.15 | 0 |
| 1 | 2 | 1 | 0.6 | 0 |
| 1 | 2 | 1 | 10 | 0.9 |
| 1 | 2 | 1.2 | 12 | 1 |
| 1 | 2 | 4 | 19 | 1.84 |

A particularly unexpected finding was that, according to the invention, it is possible in a simple and economical way to synthesize the ammonia adducts of the manganese salts by a judicious choice of the ammonia concentration and, in particular, that the molar quantities needed for the formation of ammonium dithiocarbamates are not necessary.

The products obtained are characterized by IR measurement, elemental analysis, $CS_2$ determination by the method of CIPAC Handbook, 1970, 1, p. 463 and $NH_3$ determination (titrimetric determination of the ammonia liberated with sodium hydroxide.)

When 80% manganese oxide was used, product yields of up to almost 100% were achieved; the content of ammonia-containing Maneb was as high as 85%. The resulting product mixture can be used directly.

In both procedures it is possible to use, as the manganese oxide, a manganese oxide of technical quality, which preferably has a manganese oxide content of 70 to 90 weight percent. In particular, a manganese oxide of technical quality with the following composition is used: MnO 78-80%, $MnO_2$ ca. 0.5%, $Al_2O_3$ ca. 6%, FeO ca. 5%, $SiO_2$ ca. 3%, C ca. 1%, $K_2O$ ca. 0.6%; the rest consists of a plurality of constituents in an order of magnitude of less than 0.5%. The insoluble impurities of the manganese oxide are also contained in the end product, but this is hardly a problem since the manganese salt—containing fillers—usually is available on the market anyway. However, if the impurities cause problems, it is also possible, according to the invention, to use pure manganese oxide. In both processes of the invention, the manganese oxide is used in the most finely divided form possible. It is particularly advantageous to work with a particle size of less than 125 μm. Such manganese oxide specimens can, if necessary, be obtained from the usual manganese oxide samples by grinding and sieving.

It is advantageous for the reaction to be performed with vigorous stirring in an aqueous medium. The presence of surfactants is also advantageous.

Aliphatic diamines with 2 to 6 C atoms can be used as the diamine. Preferably an aliphatic 1,2-diamine, especially ethylenediamine or propylenediamine, is used.

Both process variants have the advantage that the mother liquor can be recirculated, resulting in very substantial savings of materials. It is also possible to use technical grades of manganese oxide. The resulting product can be used directly as a fungicide. It is also possible to blend the products with other compounds, for example with zinc ethylene bisdithiocarbamate. The product obtained can also be reacted with formaldehyde.

The invention will now be explained in greater detail with reference to the following examples:

EXAMPLE 1

Synthesis of an ammonia adduct of manganese ethylene bisdithiocarbamate 2.24 moles of carbon disulfide are added, with intensive stirring, to a solution of 1.12 moles of ethylenediamine and 1.12 moles of ammonia in 232 g of water together with a few drops of Serdox NOP 9* in a glass reaction vessel while the temperature is maintained below 30° C. After 15 minutes of further stirring, 91 g of technical manganese oxide (MnO content: ca. 80%) is added and stirring is continued for 2.5 hours, during which time the temperature is raised from 40° to 50° C. as the reaction progresses.

*Nonylphenylpolyethylene glycol (Chemische Fabrik Servo b.v., Delden, The Netherlands).

Figure 1:
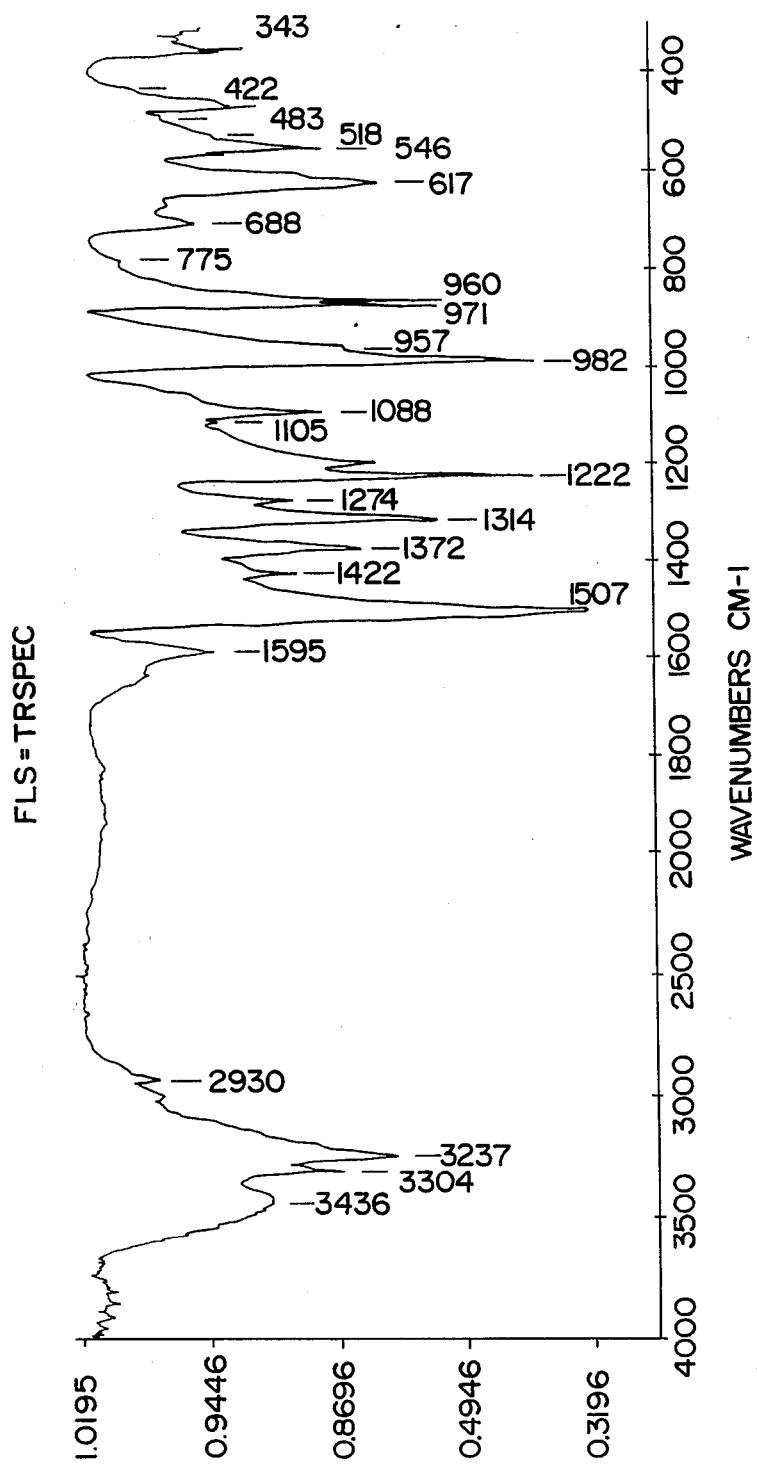
FIG. 1 shows the infrared spectrum of the ammonia adduct of manganese ethylene bisdithiocarbamate produced in Example 1.

The precipitate is filtered off, washed with water and dried at 50° C. In this way, 272 g of a product is obtained which is identical in its infrared analysis (FIG. 1) with the ammonia adduct of manganese ethylene bisdithiocarbamate (molar ratio 1:1), which is described in West German Pat. No. 1,202,266. The product purity is 85.5% (determined by $CS_2$ analysis).

| Analysis: | C | 16.3% |
|---|---|---|
| | H | 3.1% |
| | N | 13.3% |
| | $CS_2$ | 46.1% |
| | $NH_3$ | 4.1% |

In addition, the product contains small quantities of the impurities, especially the oxides of aluminum, iron and silicon,. contained in the technical manganese oxide.

The mother liquor still contains small quantities of unreacted carbon disulfide, ethylenediamine and ammonia starting materials, and therefore can be reused.

EXAMPLE 2

Synthesis of an ammonia adduct of manganese ethylene bisdithiocarbamate 2.24 moles of carbon disulfide are added, with vigorous stirring, to a solution of 1.12 moles of ethylenediamine and 1.12 moles of ammonia in 232 g of water together with a few drops of Serdox NOP 9. 101 g of technical manganese oxide (MnO content: ca. 80%) is then added and the reaction mixture is vigorously mixed for 4 hours at 40° C. The precipitate is filtered off, washed and dried. Yield: 313 g. According to infrared analysis the ammonia adduct of manganese ethylene bisdithiocarbamate is again present (purity 84.2% according to $CS_2$ analysis).

| Analysis: | C | 16.2% |
|---|---|---|
| | H | 3.0% |
| | N | 13.0% |
| | $CS_2$ | 45.4% |
| | $NH_3$ | 4.3% |

EXAMPLE 3

Synthesis of an ammonia adduct of manganese ethylene bisdithiocarbamate

An aqueous solution of ammonium ethylene bisdithiocarbamate, synthesized from 0.28 moles of ethylenediamine, 0.56 moles of carbon disulfide, 0.56 moles of ammonia and 470 g of water together with a few drops of Serdox NOP 9 (according to the example described in U.S. Pat. No. 2,844,623, column 3, line 4) is reacted while stirring with 17.1 g of technical manganese oxide (ca. 80%, MnO content ca. 0.19 moles). The reaction temperature is 50° C. and the reaction time 3 hours. The solid formed is filtered off, washed and dried. 42.4 g of a product is obtained which, according to infrared analysis, corresponds to the adduct of manganese ethylene bisdithiocarbamate with ammonia (molar ratio 1:1; content: 72.5%).

| Analysis: | C | 14.6% |
|---|---|---|
| | H | 2.7% |
| | N | 11.0% |
| | $CS_2$ | 39.0% |
| | $NH_3$ | 3.9% |

EXAMPLE 4

Synthesis of an ammonia adduct of manganese ethylene bisdithiocarbamate

To a solution consisting of 0.56 moles of ethylenediamine, 2.24 moles of ammonia and 125 g of water are added 1.12 moles of carbon disulfide with vigorous stirring, while the reaction temperature is maintained below 30° C. After 10 minutes of further stirring, 50.5 g of technical MnO (MnO content: ca. 0.56 moles) is added and stirring of the mixture is continued for 2.5 hours at 50° C. The solid is then filtered off, washed and dried, yielding 156.1 g of a product which, on the basis of its analytical data, corresponds to an adduct of manganese ethylene bisdithiocarbamate with ammonia (molar ratio 1:2; content: 81.1% according to $CS_2$ analysis).

| Analysis: | $CS_2$ | 41.3% |
|---|---|---|
| | $NH_3$ | 8.5% |

EXAMPLE 5

Synthesis of an ammonia adduct of manganese ethylene bisdithiocarbamate

An aqueous solution of ammonium ethylene bisdithiocarbamate, synthesized from 0.56 moles of ethylenediamine, 1.12 moles of carbon disulfide, 1.12 moles of ammonia and 125 g of water (according to the example described in U.S. Pat. No. 2,844,623, column 3, line 4) is reacted, with vigorous stirring, with 25 g of technical manganese oxide (80%, MnO content: ca. 0.28 moles). The reaction temperature is 50° C. and the reaction time 3 hours. The product formed is filtered off, washed with water and dried. 81.7 g of a product is obtained which, on the basis of its analytical data, corresponds to an adduct of manganese ethylene bisdithiocarbamate with ammonia (molar ratio 1:2; content: 80.2% according to $CS_2$ analysis).

| Analysis: | $CS_2$ | 40.9% |
|---|---|---|
| | $NH_3$ | 8.6% |

EXAMPLE 6

Synthesis of manganese ethylene bisdithiocarbamate

Figure 2:
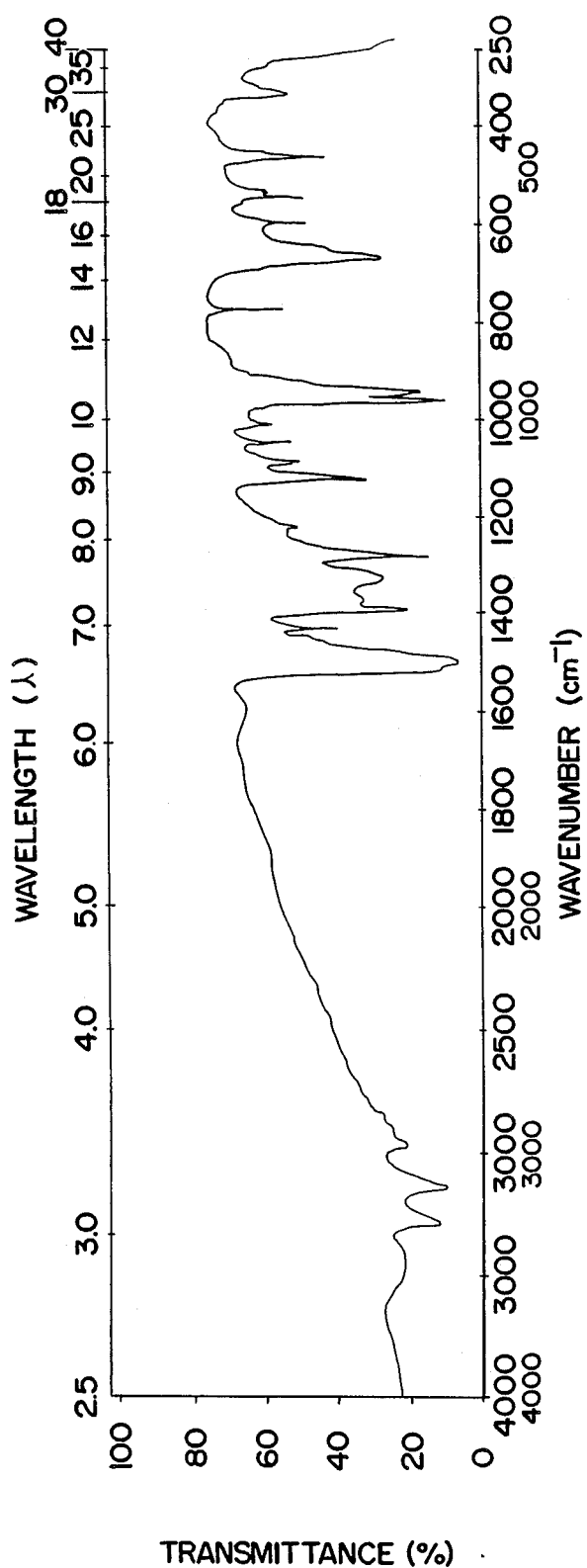
FIG. 2 shows the infrared spectrum of the manganese ethylene bisdithiocarbamate produced in Example 6.

An aqueous solution of ammonium ethylene bisdithiocarbamate, synthesized from 0.11 moles of ethylenediamine, 0.22 moles of carbon disulfide, 0.22 moles of ammonia and 720 g of water (according to the example described in U.S. Pat. No. 2,844,623, column 3, line 4) is reacted with 5.2 g of technical manganese oxide (ca. 80%, MnO content ca. 0.056 moles). The reaction temperature is 50° C. and the reaction time 3 hours. The solid is filtered off, washed and dried. In this way 13.7 g of a product was obtained which is identical in its infrared spectrum with manganese ethylene bisdithiocarbamate (FIG. 2). According to $CS_2$ analysis, the product purity is 69.8% (ammonia content: <0.1%).

EXAMPLE 7

Synthesis of manganese ethylene bisdithiocarbamate 0.44 moles of carbon disulfide are added, with vigorous stirring, to a solution consisting of 0.22 moles of ethylenediamine, 0.22 moles of ammonia and 360 g of water together with a few drops of Serdox NOP 9. After further brief stirring, 10.5 g of technical manganese oxide (80%, MnO content: ca. 0.116 moles) is added and the stirring is continued for 6 hours, during which time the temperature is raised from 40° to 50° C. as the reaction progresses. The solid is then filtered off, washed and dried. In this way, 27.4 g of a product is obtained which corresponds in its infrared spectrum to ammonia-free manganese ethylene bisdithiocarbamate (content according to $CS_2$ analysis 71.4%; ammonia content <0.1%).

EXAMPLE 8

Synthesis of an ammonia adduct of manganese propylene bisdithiocarbamate 1.12 moles of carbon disulfide are added, with vigorous stirring, to a solution of 0.56 moles of propylenediamine and 0.56 moles of ammonia in 116 g of water, while the temperature is maintained below 30° C. After 15 minutes of further stirring, 50.5 g of technical manganese oxide (ca. 80%, MnO content: ca. 0.56 moles) is added and vigorous stirring is continued for 4 hours at 40° C. The resulting solid is filtered off, washed and dried.

| Analysis: | $CS_2$ | 35.1% |
|---|---|---|
| | $NH_3$ | 2.2% |

What is claimed is:

1. A process for synthesizing adducts of alkylene bisdithiocarbamates and ammonia in a molar ratio of $1/\leqq 2$, comprising reacting a metal compound selected from the group consisting of manganese (II) oxide and the hydrate and hydroxide thereof with an aqueous mixture of an alkylenediamine, carbon disulfide and ammonia in water using 2 moles or less of ammonia per mole of alkylenediamine.

2. The process according to claim 1, wherein said aqueous mixture of alkylenediamine, carbon disulfide and ammonia has a molar ratio of $\frac{1}{2}/0.5-1$, respectively, and is reacted with said metal compound to synthesize an adduct of ammonia and manganese alkylene bisdithiocarbamate in a molar ratio of 0.8-1.2/1, and said process further comprises adjusting the quantity of water so that the ammonia concentration is higher than 1 mole per liter of water.

3. The process according to claim 1, wherein said aqueous mixture of alkylenediamine, carbon disulfide and ammonia has a molar ratio of $\frac{1}{2}$/less than 2, respectively, and is reacted with said metal compound to synthesize an adduct of ammonia and manganese alkylene bisdithiocarbamate in a molar ratio of 1.6-2/1, and said process further comprises adjusting the quantity of water so that the ammonia concentration is higher than 1 mole per liter of water.

4. The process according to claim 1, wherein the alkylenediamine is an aliphatic diamine with 2 to 6 carbon atoms and primary amino groups.

5. The process according to claim 1, wherein the alkylenediamine is ethylenediamine.

6. The process according to claim 1, wherein the alkylenediamine is propylenediamine.

7. The process according to claim 1, wherein the manganese oxide is of technical quality with a MnO content of 70 to 90%.

* * * * *